United States Patent [19]

Naruse et al.

[11] Patent Number: 4,783,565
[45] Date of Patent: Nov. 8, 1988

[54] SELECTIVE PREPARATION OF CIS-PERHYDROACENAPHTHENE

[75] Inventors: Yoshihiro Naruse; Toshihide Suzuki, both of Chiba, Japan

[73] Assignee: Kawasaki Steel Corporation, Kobe, Japan

[21] Appl. No.: 45,578

[22] Filed: May 4, 1987

[30] Foreign Application Priority Data

May 12, 1986 [JP] Japan .................. 61-107969

[51] Int. Cl.$^4$ ........................... C07C 5/10
[52] U.S. Cl. .................... 585/268; 585/266; 585/267; 585/269
[58] Field of Search ............... 585/266, 267, 268, 269

[56] References Cited

U.S. PATENT DOCUMENTS

| | | | |
|---|---|---|---|
| 3,128,316 | 4/1964 | Schneider | 585/352 |
| 3,183,278 | 5/1965 | Koch | 585/268 |
| 3,349,140 | 10/1967 | Weitkamp | 585/268 |
| 4,046,824 | 9/1977 | Ransley | 585/269 |
| 4,329,529 | 5/1982 | Nambu | 585/268 |

FOREIGN PATENT DOCUMENTS 0164038 12/1985 European Pat. Off. .

OTHER PUBLICATIONS

"Preparation of Diamondoid Hydrocarbons by Rearrangement Employing a Chlorinated Platinum–Alumina Catalyst", *Journal of the American Chemical Society*, by D. E. Johnston et al., Jun. 2, 1971, pp. 2798 and 2799.

Primary Examiner—Patrick P. Garvin
Assistant Examiner—George R. Fourson
Attorney, Agent, or Firm—Young & Thompson

[57] ABSTRACT

A cis-isomer of perhydroacenaphthene is selectively prepared through hydrogenation of acenaphthene by effecting hydrogenation of 80° to 200° C. in the presence of a Ru and/or Rh based catalyst. A cis-isomer having the highest boiling point is obtained as a major product.

7 Claims, 1 Drawing Sheet

SELECTIVE PREPARATION OF CIS-PERHYDROACENAPHTHENE

BACKGROUND OF THE INVENTION

This invention relates to the preparation of perhydroacenaphthene useful as a high boiling oil by hydrogenating acenaphthene. More particularly, it relates to a process for selectively preparing cis-perhydroacenaphthene in pure form rather than as a mixture of isomers, which can be subsequently used as an intermediate for such chemical reaction as synthesis of adamantanes without incurring any difference in reaction route, activation energy, and reaction yield.

It is well known in the art to hydrogenate a polycyclic aromatic compound in an atmosphere of pressurized hydrogen in the presence of a noble metal-based catalyst such as Pt and Pd catalysts or a nickel-based catalyst such as Raney nickel and nickel/kieselguhr catalysts to eventually produce a corresponding perhydro compound.

For acenaphthene, it is well known that by hydrogenating acenaphthene in the presence of a Raney nickel catalyst, perhydroacenaphthene is produced by way of tetrahydroacenaphthene. As described in the literature (see J. Am. Chem. Soc., June 2, 1971, 2798), four stereoisomers are known for perhydroacenaphthene. The detail of these four isomers has not been generally investigated and no attempt has been made to selectively synthesize a particular isomer. Consequently, perhydroacenaphthene is usually available as a mixture of four isomers. It has never been attempted to selectively synthesize a particular isomer or a particular group of isomers.

No problem is encountered with an isomer mixture when perhydroacenaphthene is merely used as a high-boiling oil. It is, however, desirable to selectively synthesize a particular isomer or a particular group of isomers in using perhydroacenaphthene as an intermediate for chemical reaction to a final product because the reaction route and the activation energy involved in the reaction vary with isomers, resulting in varying reaction yields. As far as the literature and patent publications are concerned, no such concept about perhydroacenaphthene has been reported.

The Raney nickel used for hydrogenation requires a solvent for certain starting materials and is inconvenient because of short life and the need for careful handling.

SUMMARY OF THE INVENTION

An object of the present invention is to provide a novel process for selectively preparing perhydroacenaphthene in high yields.

Another object of the present invention is to provide a novel process for selectively preparing a particular isomer of perhydroacenaphthene, especially a cis-isomer having the highest boiling point as a main product.

Perhydroacenaphthene is useful as an intermediate for the synthesis of medical compounds. We have discovered that in producing perhydroacenaphthene for such destination by hydrogenating acenaphthene in the presence of various hydrogenating catalysts, the ratio of the four isomers of perhydroacenaphthene produced can be controlled to a significant extent b a choice of the catalyst and reaction conditions.

According to the present invention, there is provided a process for selectively preparing cis-perhydroacenaphthene by hydrogenating acenaphthene, characterized by effecting the hydrogenation reaction at a temperature of 80° to 200° C. in the presence of a Ru based catalyst and/or a Rh based catalyst, producing a cis-isomer having the highest boiling point as a major product.

BRIEF DESCRIPTION OF THE DRAWING

The invention will be more fully understood by reading the following detailed description taken in conjunction with the accompanying drawing, in which.

the only figure.

DETAILED DESCRIPTION OF THE INVENTION

Figure 1:
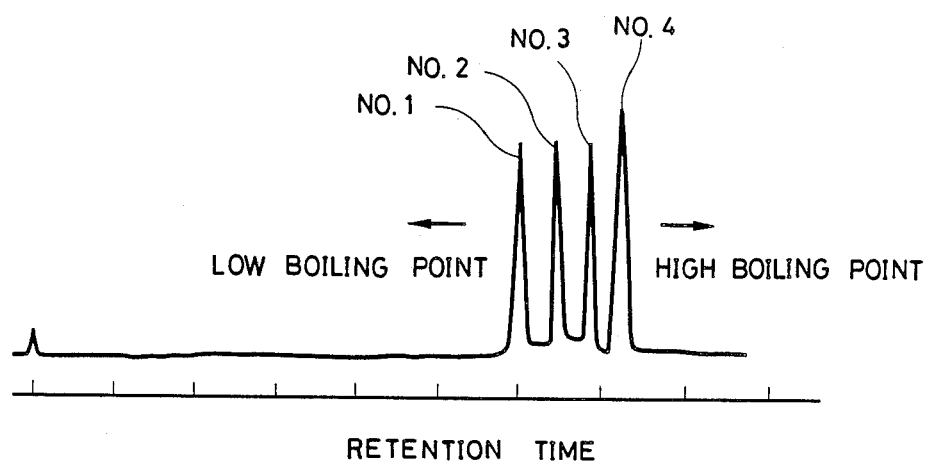
FIG. 1 is a gas chromatogram of a mixture of four isomers of perhydroacenaphthene.

Hydrogenation reaction of acenaphthene proceeds as follows.

acenaphthene —hydrogenation→ perhydroacenaphthene

Four isomers are The isomers can be identified by, for example, the analysis chart obtained by gas chromatography using a packing material of the nature allowing materials to elute in the order of their boiling point. Based on a series of analysis results, it is supposed that peak Nos. 1 and 3 in FIG. 1 are attributable to trans-isomers and peak Nos. 2 and 4 are cis-isomers. The conditions used in determining the gas chromatogram of FIG. 1 are shown below.

Column: silicon OV-17, 2 m (dual)
Detector: FID detector
Initial temperature: 70° C., 4 minutes hold
Heating rate: 6° C./min.
Final temperature: 250° C., 16 minutes hold The process of the present invention selectively prepares a perhydroacenaphthene isomer corresponding to No. 4 peak in FIG. 1, that is, a cis-isomer having the highest boiling point.

Typical prior art methods for preparing a mixture of four isomers of perhydroacenaphthene are by subjecting acenaphthene to hydrogenation reaction in the presence of a catalyst under a hydrogen pressure of about 100 to 200 kg/cm$^2$ at a temperature of about 100° to 300° C. for several hours. Useful are catalysts comprising a carrier such as carbon and alumina having a noble metal such as Pd or Pt carried thereon and/or nickel-based catalysts such as Raney nickel.

Making a further study on the preparation of perhydroacenaphthene from acenaphthene with the aid of various hydrogenating catalysts, we have discovered that a particular perhydroacenaphthene can be produced in a high yield and a high selectivity by carrying out the hydrogenation reaction under certain conditions using a specific catalyst.

In order to preferentially produce a perhydroacenaphthene isomer corresponding to No. 4 peak in the gas chromatogram of FIG. 1, that is, the high boiling cis-isomer, it is recommended to hydrogenate acenaphthene under a hydrogen pressure of 100 to 200 kg/cm$^2$ gauge at a temperature of 80° to 200° C., more preferably 100° to 180° C. using a Ru and/or Rh based catalyst.

The reaction can proceed at temperatures of lower than 80° C., but at a very low rate. At reaction temperatures of higher than 200° C., other isomers are produced in larger amounts, resulting in a reduced selectivity.

Any Ru and/or Rh based catalysts may be used. Typical are carbon carried catalysts such as Ru/C and Rh/C catalysts having ruthenium and rhodium on a carbon carrier, respectively. The amount of the catalyst charged may be such that at least 0.025% by weight of metallic Ru and/or Rh is present based on the weight of acenaphthene. Catalyst amounts of 0.025 to 0.10% of Ru and/or Rh based on the weight of acenaphthene are preferred because the reaction rate is proportional to the catalyst charge. Metallic Ru and/or Rh leadings of 0.025 to 0.10% by weight correspond to catalyst charges of 0.5 to 2% when the catalyst contains 5% of Ru and/or Rh as is usually the case. With more than 2% by weight of the 5% Ru and/or Rh catalyst, a rapid reaction will take place to undesirably bring a quick rise of reaction temperature. The reaction time generally ranges from about 20 minutes to about 4 hours although it varies with the catalyst charge and the reaction temperature. A reaction time within 2 hours is sufficient for reaction at a temperature of about 200° C. The reaction time corresponds to the minimum time taken for the necessary hydrogen consumption since 5 moles of hydrogen must be consumed per mole of acenaphthene in order that acenaphthene reacts with hydrogen to form perhydroacenaphthene.

EXAMPLES

Examples of the present invention are presented below by way of illustration and not by way of limitation. All percents are by weight unless otherwise stated. Nos. 1 to 4 isomers are identified in the gas chromatogram of FIG. 1.

EXAMPLE 1

An induction agitator-equipped autoclave having an internal volume of about 150 ml was charged with 50 grams of acenaphthene and 1 gram of a 5% Ru/C catalyst and with hydrogen at an initial pressure of 150 kg/cm$^2$ gauge. Reaction was effected at 100° C. for 3 hours. During reaction, samples were taken out at intervals and analyzed for product composition by gas chromatography. No further change was observed in product composition at the end of 2 hour reaction.

The temperature was increased to about 150° C. at the initial stage of reaction, but restored to the initial set temperature of 100° C. at the end of 1½ hour reaction.

The final hydrogenated product has the composition containing 0.06% of No. 1 isomer, 1.2% of No. 2 isomer, 3.91% of No. 3 isomer, 93.96% of No. 4 isomer, and 0.87% of partially hydrogenated and unreacted acenaphthene.

Based on the results, the percent conversion from acenaphthene to perhydroacenaphthene was 99.13% and the selectivity of No. 4 or high boiling cis-isomer was about 95%.

EXAMPLES 2-3

Acenaphthene was hydrogenated by the same procedure as in Example 1 except that the amount of the catalyst charged and the reaction time were changed.

Example 2 continued reaction for 70 minutes using 0.5 grams of the 5% Ru/C catalyst. At the end of 60 minute reaction, no further change was observed in hydrogen pressure and product composition.

Example 3 continued reaction for 130 minutes using 0.25 grams of the 5% Ru/C catalyst. At the end of 120 minute reaction, no further change was observed in hydrogen pressrre and product composition.

In both Examples 2 and 3, perhydroacenaphthene was produced in a yield of more than 99% and contained 0.15% of No. 1 isomer, 1.05% of No. 2 isomer, and 5.80% of No. 3 isomer, indicating a selectivity of No. 4 or high boiling cis-isomer of 92% or higher.

EXAMPLE 4

A shaking autoclave having an internal volume of about 60 ml was charged with 5 grams of acenaphthene and 0.1 gram of a 5% Ru/C catalyst and with hydrogen at an initial pressure of 134 kg/cm$^2$ gauge. Reaction was effected at 200° C. for 4 hours.

Perhydroacenaphthene was produced in a yield of 100%, containing 1.1% of No. 1 isomer, 3.5% of No. 2 isomer, and 7.4% of No. 3 isomer, indicating a selectivity of No. 4 isomer of 88%.

EXAMPLE 5

Acenaphthene was hydrogenated by the same procedure as in Example 4 except that the catalyst was replaced by a 5% Rh/C catalyst and reaction was effected at 150° C. for 30 minutes. Perhydroacenaphthene was produced in a yield of 100%, containing 1.1% of No. 1 isomer, 3.6% of No. 2 isomer, and 4.4% of No. 3 isomer, indicating a selectivity of No. 4 isomer of 90.9%.

EXAMPLE 6

Acenaphthene was hydrogenated by the same procedure as in Example 4 except that the catalyst was replaced by a 0.5% Rh/Al$_2$O$_3$ catalyst and reaction was effected at 125° C. for 40 minutes. Perhydroacenaphthene was produced in a yield of 100%, containing 3.4% of No. 1 isomer, 4.7% of No. 2 isomer, and 4.1% of No. 3 isomer, indicating a selectivity of No. 4 isomer of 89.7%.

COMPARATIVE EXAMPLE

Acenaphthene was hydrogenated by the same procedure as in Example 1 except that the catalyst was replaced by a 5% Pd/C catalyst and reaction was effected at 160° C. for 6 hours. No substantial change was observed in the distribution of reaction products at the end of 4 hour reaction. Perhydroacenaphthene was finally obtained in a yield of 99.6%. The yields of Nos. 1 to 4 isomers were 33.5%, 11.8%, 24.5%, and 29.7%, respectively.

In producing perhydroacenaphthene by hydrogenating acenaphthene, the process of the present invention can successfully produce perhydroacenaphthene in high yields and selectively obtain a cis-isomer having the highest boiling point by employing a proper catalyst and reaction conditions.

Perhydroacenaphthene is used not only as high boiling oil and traction drive oil, but also as an intermediate for the production of adamantanes. In the latter case, the possible selective preparation of a particular isomer in high yields according to the present invention offers a very useful reaction intermediate which ensures efficient synthesis of the destined product without incurring any variation in reaction route, activation energy and reaction yield.

We claim:

1. A process for selectively preparing cis-perhydroacenaphthene by hydrogenating acenaphthene, characterized by effecting the hydrogenation reaction at a temperature of 80° to 200° C. in the presence of a metallic Rh catalyst supported on a carrier, producing a cis-isomer having the highest boiling point as a major product.

2. The process of claim 1 wherein the reaction temperature ranges from 100° to 180° C.

3. The process of claim 1 wherein the reaction is effected under a hydrogen pressure of 100 to 200 kg/cm$^2$.

4. The process of claim 1 wherein the reaction is continued for about 20 minutes to about 4 hours.

5. The process of claim 1 wherein the catalyst is present in an amount to provide 0.025 to 0.1% of Rh metal based on the weight of acenaphthene 6. The process of claim 1 wherein the carrier is carbon.

7. The process of claim 1 wherein teh carrier is alumina.

* * * * *